US011084889B2

(12) United States Patent
Matsubara et al.

(10) Patent No.: US 11,084,889 B2
(45) Date of Patent: Aug. 10, 2021

(54) WATER-ABSORBENT RESIN PARTICLES AND METHOD FOR PRODUCING SAME

(71) Applicant: SDP Global Co., Ltd., Tokyo (JP)

(72) Inventors: Yusuke Matsubara, Tokyo (JP); Toru Miyajima, Tokyo (JP)

(73) Assignee: SDP Global Co., Ltd., Tokyo (JP)

(*) Notice: Subject to any disclaimer, the term of this patent is extended or adjusted under 35 U.S.C. 154(b) by 17 days.

(21) Appl. No.: 15/764,962

(22) PCT Filed: Sep. 30, 2016

(86) PCT No.: PCT/JP2016/079081
§ 371 (c)(1),
(2) Date: Mar. 30, 2018

(87) PCT Pub. No.: WO2017/057706
PCT Pub. Date: Apr. 6, 2017

(65) Prior Publication Data
US 2018/0282441 A1 Oct. 4, 2018

(30) Foreign Application Priority Data

Oct. 2, 2015 (JP) .............................. JP2015-196606

(51) Int. Cl.
| | | |
|---|---|---|
| *C08F 2/44* | (2006.01) | |
| *C08F 220/06* | (2006.01) | |
| *C08F 4/40* | (2006.01) | |
| *C08J 3/12* | (2006.01) | |
| *A61L 15/26* | (2006.01) | |
| *A61F 13/53* | (2006.01) | |
| *A61L 15/60* | (2006.01) | |
| *B01J 31/12* | (2006.01) | |
| *C08F 220/56* | (2006.01) | |
| *C08K 5/56* | (2006.01) | |
| *C08K 5/59* | (2006.01) | |

(52) U.S. Cl.
CPC .............. *C08F 2/44* (2013.01); *A61F 13/53* (2013.01); *A61L 15/26* (2013.01); *A61L 15/60* (2013.01); *B01J 31/122* (2013.01); *C08F 4/40* (2013.01); *C08F 220/06* (2013.01); *C08F 220/56* (2013.01); *C08J 3/12* (2013.01); *C08K 5/56* (2013.01); *C08K 5/59* (2013.01); *A61F 2013/530481* (2013.01); *B01J 2531/52* (2013.01); *B01J 2531/54* (2013.01); *B01J 2531/60* (2013.01)

(58) Field of Classification Search
CPC ..................... C08F 4/44; C08F 2/44
See application file for complete search history.

(56) References Cited

U.S. PATENT DOCUMENTS

| | | | | | |
|---|---|---|---|---|---|
| 4,085,168 | A | * | 4/1978 | Milkovich | ............ C08F 290/02 523/106 |
| 4,666,983 | A | * | 5/1987 | Tsubakimoto | .......... A61L 15/60 525/119 |
| 7,276,569 | B2 | * | 10/2007 | Yamago | ................ C07C 395/00 526/343 |
| 7,847,043 | B2 | * | 12/2010 | Yamago | .................... C07F 9/94 526/190 |
| 2003/0078349 | A1 | * | 4/2003 | Tagawa | ............. A61F 13/15203 526/89 |
| 2009/0281263 | A1 | * | 11/2009 | Mosler | ..................... B01J 8/008 526/317.1 |
| 2012/0231060 | A1 | * | 9/2012 | Coady | .................... A01N 33/12 424/402 |
| 2014/0309328 | A1 | * | 10/2014 | Abdul | .................... C08G 18/10 523/106 |
| 2018/0318792 | A1 | * | 11/2018 | Miyajima | ................ C08K 3/00 |

FOREIGN PATENT DOCUMENTS

| | | |
|---|---|---|
| JP | 53-046389 A | 4/1978 |
| JP | 55-133413 A | 10/1980 |
| JP | 56-026909 A | 3/1981 |
| JP | 03-179008 A | 8/1991 |
| JP | 07-088171 A | 4/1995 |
| JP | 2001-129311 A | 5/2001 |
| JP | 2001-354721 A | 12/2001 |
| JP | 2003-165883 A | 6/2003 |

(Continued)

OTHER PUBLICATIONS

Machine translation of JP 2012-206038 (Year: 2019).*
Machine Translation of JP 2013-231199, 2019 (Year: 2019).*
Yamago, Journal of Polymer Science: Part A: Polymer Chemistry, vol. 44, 1-12 (2006) (Year: 2006).*

(Continued)

*Primary Examiner* — Liam J Heincer
(74) *Attorney, Agent, or Firm* — Locke Lord LLP; James E. Armstrong, IV; Nicholas J. DiCeglie, Jr.

(57) ABSTRACT

Provided is a method for producing water-absorbent resin particles, which is capable of improving the gel strength for the purpose of achieving a good balance between the absorption under load and the rate of liquid permeation through gel. The present invention is a method for producing water-absorbent resin particles, which is characterized by comprising a step wherein a monomer composition containing a water-soluble vinyl monomer (a1) and/or a vinyl monomer (a2) that turns into a water-soluble vinyl monomer (a1) by means of hydrolysis and a crosslinking agent (b) is polymerized in the presence of at least one organic main group element compound selected from the group consisting of organic iodine compounds, organic tellurium compounds, organic antimony compounds, and organic bismuth compounds.

4 Claims, 2 Drawing Sheets

(56) References Cited

FOREIGN PATENT DOCUMENTS

| | | |
|---|---|---|
| JP | 2003-225565 A | 8/2003 |
| JP | 2005-075982 A | 3/2005 |
| JP | 2005-097569 A | 4/2005 |
| JP | 3648553 B2 | 5/2005 |
| JP | 2006-131767 A | 5/2006 |
| JP | 2012-206038 A | 10/2012 |
| JP | 2013-231199 A | 11/2013 |
| WO | 2004/014848 A1 | 2/2004 |
| WO | 2006/062255 A1 | 6/2006 |
| WO | 2007/119884 A1 | 10/2007 |
| WO | 2011/016166 A1 | 2/2011 |

OTHER PUBLICATIONS

Wang et al. (Journal of Polymer Science, Part A: Polymer Chemistry 2013, 51, 1872-1879) (Year: 2013).*
International Search Report dated Nov. 8, 2016, issued for PCT/JP2016/079081.

* cited by examiner

WATER-ABSORBENT RESIN PARTICLES AND METHOD FOR PRODUCING SAME

CROSS REFERENCE TO RELATED APPLICATIONS

This application is related to co-pending application: "ABSORBENT RESIN COMPOSITION AND METHOD FOR PRODUCING SAME" filed even date herewith in the names of Toru MIYAJIMA, Yusuke MATSUBARA, Taichi MATSUYAMA and Shoichi HIROOKA as a national phase entry of PCT/JP2016/079085, which application is assigned to the assignee of the present application and is incorporated by reference herein.

TECHNICAL FIELD

The present invention relates to a water-absorbent resin particle and a method for the production thereof.

BACKGROUND ART

Conventionally, hydrophilic crosslinked polymers called water-absorbent resins are used as a powdery absorbent having absorption performance to aqueous liquids, and their application range has been expanded to applications in various industrial fields, such as sanitary goods, e.g., disposable diaper and sanitary items, a dew-condensation preventing agent, and an agricultural and horticultural water retention agent. Water-absorbent resins to be used for such applications are desired to be high in water retention capacity and gel strength.

It is known that the water absorption performance (water retention capacity) under normal pressure of a water-absorbent resin is proportional to "(ion osmotic pressure+affinity of polymer chain to water)/crosslinking density of polymer" and the crosslinking density contributes to the performance of a water-absorbent resin. Therefore, reducing the amount of a crosslinking agent used is usually performed as means for increasing water retention capacity, and there is known as means for further improving the performance of a water-absorbent resin particle a method of performing aqueous solution-polymerizing a monomer composition comprising a radical polymerizable monomer and a crosslinking agent in the presence of a chain transfer agent (see, for example, Patent Literature 1).

PRIOR ART DOCUMENTS

Patent Documents

Patent Document 1: JP-A-3-179008

SUMMARY OF THE INVENTION

Problems to be Solved by the Invention

However, the method in which a chain transfer agent is used as disclosed in Patent Literature 1 merely affords an insufficient gel strength though it has some effect on improvement in water retention capacity. Since gel strength influences the amount of absorption under load and gel liquid permeation rate, it is required in sanitary goods applications such as disposable diapers to further improve gel strength in order to be compatible with the amount of absorption under load and the gel liquid permeation rate.

Solutions to the Problems

The present inventors have accomplished the present invention as a result of earnest studies performed for attaining the above-mentioned object.

That is, the present invention relates to a method for producing water-absorbent resin particles, comprising a step of polymerizing a monomer composition comprising a water-soluble vinyl monomer (a1) and/or a vinyl monomer (a2) that turns into a water-soluble vinyl monomer (a1) through hydrolysis and a crosslinking agent (b) in the presence of at least one organic main group element compound selected from the group consisting of organic iodine compounds, organic tellurium compounds, organic antimony compounds, and organic bismuth compounds; and a water-absorbent resin particle comprising a crosslinked polymer (A) containing a water-soluble vinyl monomer (a1) and/or a vinyl monomer (a2) that turns into a water-soluble vinyl monomer (a1) through hydrolysis and a crosslinking agent (b) as essential constituent units, wherein the water-absorbent resin particle contains at least one main group element selected from the group consisting of iodine, tellurium, antimony, and bismuth in a content of 0.0005 to 0.1% by weight based on the weight of the water-absorbent resin particle.

Advantages of the Invention

Water-absorbent resin particles obtained by the production method of the present invention and the water-absorbent resin particles of the present invention have high gel strength at the time of water absorption and are superior in the amount of absorption under load and gel liquid permeation rate. Therefore, water-absorbent resin particles obtained by the production method of the present invention and the water-absorbent resin particles of the present invention exert excellent absorption performance (e.g., liquid diffusion property, absorption rate, and the amount of absorption) stably under various use conditions and the sanitary goods that use there are less prone to cause skin irritation.

MODE FOR CARRYING OUT THE INVENTION

Figure 1:
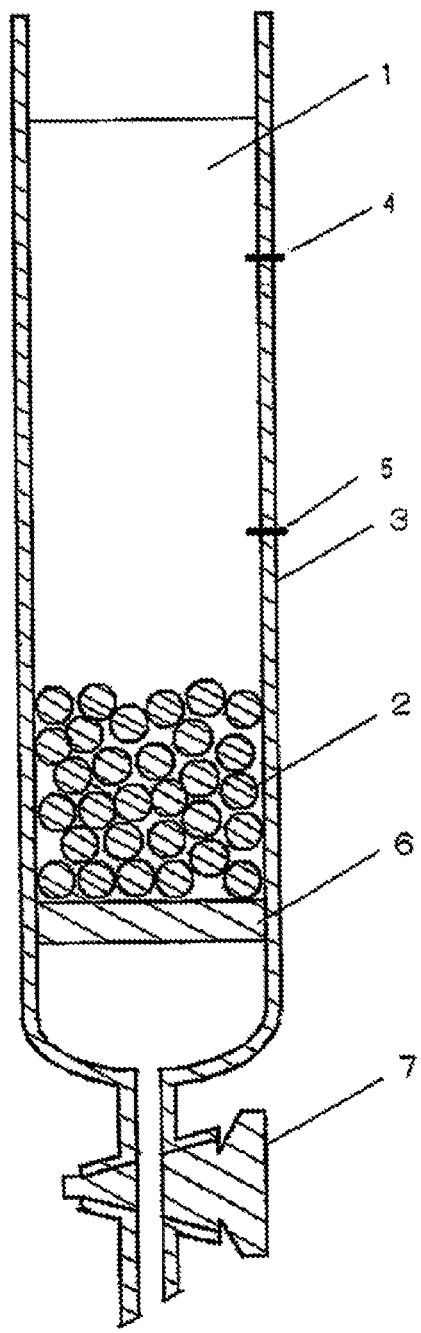
FIG. 1 is a drawing schematically illustrating a cross-sectional view of a filtration cylinder for measuring a gel liquid permeation rate.

The production method of the present invention has a step of polymerizing a monomer composition comprising a water-soluble vinyl monomer (a1) and/or a hydrolyzable vinyl monomer (a2) and a crosslinking agent (b) in the presence of at least one organic main group element compound selected from the group consisting of organic iodine compounds, organic tellurium compounds, organic antimony compounds, and organic bismuth compounds (hereinafter also merely referred to as organic main group element compound).

In the production method of the present invention, the exact chemical action or effect of organic main group element compounds is unknown, but it is presumed that an organic main group element compound serves as a dormant for radical polymerization and the uniformity of a gel is improved by performing radical polymerization in the presence of the organic main group element compound and, as a result, the water retention capacity and the gel strength are improved.

The water-soluble vinyl monomer (a1) as used in the production method of the present invention is not particularly limited, and there can be used such conventional monomers as vinyl monomers having at least one water-soluble substituent and an ethylenically unsaturated group disclosed in paragraphs 0007 to 0023 of Japanese Patent No. 3648553 (e.g., anionic vinyl monomers, nonionic vinyl monomers, and cationic vinyl monomers), the anionic vinyl monomers, and nonionic vinyl monomers, cationic vinyl monomers disclosed in paragraphs 0009 to 0024 of JP-A-2003-165883, and vinyl monomers having at least one group selected from the group consisting of a carboxy group, a sulfo group, a phosphono group, a hydroxy group, a carbamoyl group, an amino group, and an ammonio group disclosed in paragraphs 0041 to 0051 of JP-A-2005-75982.

The vinyl monomer (a2) that turns into a water-soluble vinyl monomer (a1) through hydrolysis [herein, also referred to as hydrolyzable vinyl monomer (a2)] is not particularly limited, and there can be used such conventional vinyl monomers as vinyl monomers having at least one hydrolyzable substituent that turns into a water-soluble substituent through hydrolysis disclosed in paragraphs 0024 to 0025 of Japanese Patent No. 3648553, and vinyl monomers having at least one hydrolyzable substituent [e.g., a 1,3-oxo-2-oxapropylene (—CO—O—CO—) group, an acyl group, and a cyano group] disclosed in paragraphs 0052 to 0055 of JP-A-2005-75982. The water-soluble vinyl monomer as used herein means a vinyl monomer soluble in an amount of at least 100 g in 100 g of water at 25° C. The hydrolyzability of the hydrolyzable vinyl monomer (a2) means a property to be hydrolyzed by the action of water and, according to need, of a catalyst (e.g., an acid or a base), thereby becoming water-soluble. Although the hydrolysis of the hydrolyzable vinyl monomer (a2) may be carried out during polymerization, after polymerization, or both during and after polymerization, after polymerization is preferred from the viewpoint of the absorption performance of water-absorbent resin particles to be obtained.

Among these, preferred from the viewpoint of absorption performance and the like are water-soluble vinyl monomers (a1), more preferred are anionic vinyl monomers and vinyl monomers having a carboxy (salt) group, a sulfo (salt) group, an amino group, a carbamoyl group, an ammonio group, or a mono-, di- or tri-alkylammonio group, even more preferred are vinyl monomers having a carboxy (salt) group or a carbamoyl group, particularly preferred are (meth)acrylic acid (salts) and (meth)acrylamide, more particularly preferred are (meth)acrylic acid (salts), and most preferred are acrylic acid (salts).

The "carboxy (salt) group" means a "carboxy group" or a "carboxylate group", and the "sulfo (salt) group" means a "sulfo group" or a "sulfonate group." The (meth)acrylic acid (salt) means acrylic acid, a salt of acrylic acid, methacrylic acid, or a salt of methacrylic acid and the (meth)acrylamide means acrylamide or methacrylamide. Examples of such salts include salts of alkali metal (lithium, sodium, potassium, etc.), salts of alkaline earth metal (magnesium, calcium, etc.), and ammonium ($NH_4$) salts. Among these salts, salts of alkali metals and ammonium salts are preferred from the viewpoint of absorption performance and the like, salts of alkali metals are more preferred, and sodium salts are particularly preferred.

When one of a water-soluble vinyl monomer (a1) and a hydrolyzable vinyl monomer (a2) is contained as a constitutional unit, a single species of each of the monomers may be contained as a constitutional unit or, alternatively, two or more species may be contained as constitutional units, according to need. The same also applies to the case where both a water-soluble vinyl monomer (a1) and a hydrolyzable vinyl monomer (a2) are contained as constitutional units. When both the water-soluble vinyl monomer (a1) and the hydrolyzable vinyl monomer (a2) are contained as constitutional units, their contained molar ratio [(a1)/(a2)] is preferably from 75/25 to 99/1, more preferably from 85/15 to 95/5, particularly preferably from 90/10 to 93/7, and most preferably from 91/9 to 92/8. Within such ranges, further improved absorption performance is achieved.

In addition to the water-soluble vinyl monomer (a1) and the hydrolyzable vinyl monomer (a2), the absorbent resin particles can contain as a constitutional unit an additional vinyl monomer (a3) copolymerizable with the aforementioned vinyl monomers. The additional vinyl monomer (a3) may be used singly or two or more of the same may be used in combination.

The additional copolymerizable vinyl monomer (a3) is not particularly limited and conventional hydrophobic vinyl monomers (e.g., hydrophobic vinyl monomers disclosed in paragraphs 0028 to 0029 of Japanese Patent No. 3648553, vinyl monomers disclosed in paragraph 0025 of JP-A-2003-165883 and paragraph 0058 of JP-A-2005-75982) can be used, and specifically, for example, the following vinyl monomers (i) to (iii) can be used.

(i) Aromatic Ethylenic Monomers Having 8 to 30 Carbon Atoms

Styrenes, such as styrene, α-methylstyrene, vinyltoluene, and hydroxystyrene, vinylnaphthalene, and halogenated forms of styrene, such as dichlorostyrene, etc.

(ii) Aliphatic Ethylenic Monomers Having 2 to 20 Carbon Atoms

Alkenes (e.g., ethylene, propylene, butene, isobutylene, pentene, heptene, diisobutylene, octene, dodecene, and octadecene), and alkadienes (e.g., butadiene and isoprene), etc.

(iii) Alicyclic Ethylenic Monomers Having 5 to 15 Carbon Atoms

Monoethylenically unsaturated monomers (e.g., pinene, limonene, and indene); and polyethylenic vinyl monomers (e.g., cyclopentadiene, bicyclopentadiene, and ethylidene norbornene), etc.

From the viewpoint of absorption performance and the like, the content (mol %) of the additional vinyl monomer (a3) unit, based on the total number of moles of the water-soluble vinyl monomer (a1) unit and the hydrolyzable vinyl monomer (a2) unit, is preferably 0 to 5, more preferably 0 to 3, even more preferably 0 to 2, and particularly preferably 0 to 1.5, and from the viewpoint of absorption performance and the like, the content of the additional vinyl monomer (a3) is most preferably 0 mol %.

The crosslinking agent (b) is not particularly limited, and conventional crosslinking agents (e.g., crosslinking agents having two or more ethylenically unsaturated groups disclosed in paragraphs 0031 to 0034 of Japanese Patent No. 3648553, crosslinking agents having at least two functional group capable of reacting with a water-soluble substituent and having at least one ethylenically unsaturated group and crosslinking agents having at least two functional groups each capable of reacting a water-soluble substituent, crosslinking agents having two or more ethylenically unsaturated groups disclosed in paragraphs 0028 to 0031 of JP-A-2003-165883, crosslinking agents having an ethylenically unsaturated group and a reactive functional group and crosslinking agents having two or more reactive substituents, crosslinkable vinyl monomers disclosed in paragraph 0059 of JP-A-2005-75982 and crosslinkable vinyl monomers disclosed in paragraphs 0015 to 0016 of JP-A-2005-95759) can be used. Among these, from the viewpoint of absorption performance and the like, crosslinking agents having two or more ethylenically unsaturated groups are preferred; triallyl cyanurate, triallyl isocyanurate, and poly(meth)allyl ethers of polyols having 2 to 10 carbon atoms are more preferred; triallyl cyanurate, triallyl isocyanurate, tetraallyloxyethane, and pentaerythritol triallyl ether are particularly preferred; and pentaerythritol triallyl ether is most preferred. The crosslinking agent (b) may be used singly or two or more of the same may be used in combination.

The content (mol %) of the crosslinking agent (b) units is preferably 0.001 to 5, more preferably 0.005 to 3, and particularly preferably 0.01 to 1 based on the total number of moles of the water-soluble vinyl monomer (a1) units and the hydrolyzable vinyl monomer (a2) units or, in the case where the additional vinyl monomer (a3) is used, the total number of moles of (a1) to (a3). Within such ranges, the absorption performance is further improved.

In the production method of the present invention, the organic main group element compound is at least one compound selected from the group consisting of organic iodine compounds, organic tellurium compounds, organic antimony compounds, and organic bismuth compounds. The organic iodine compounds, the organic tellurium compounds, the organic antimony compounds, and the organic bismuth compounds may be any organic main group element compound that serves as a dormant for radical polymerization; the organic iodine compounds disclosed as dormants in WO 2011/016166, the organic tellurium compounds disclosed in WO 2004/014848, the organic antimony compounds disclosed in WO 2006/001496, the organic bismuth compounds disclosed in WO 2006/062255, etc. can be used. Especially from the viewpoint of reactivity, the organic main group element compounds represented by the following formula (1) are preferred.

Such organic main group element compounds may be used either singly or in a combination of two or more species.

[Chemical Formula 1]

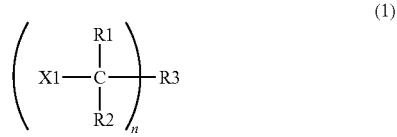

(1)

In the formula (1), $R^1$ and $R^2$ each independently represent a hydrogen atom, a saturated hydrocarbon group having 1 to 7 carbon atoms, or a monovalent group having 1 to 7 carbon atoms and having at least one non-addition-polymerizable double bond or at least one non-addition-polymerizable triple bond and $R^3$ represents an n-valent saturated hydrocarbon group having 1 to 6 carbon atoms or an n-valent group having 2 to 12 carbon atoms and having at least one non-addition-polymerizable double bond or at least one non-addition-polymerizable triple bond, provided that at least one of $R^1$ to $R^3$ in one molecule is a corresponding group having a non-addition-polymerizable double bond or at least one non-addition-polymerizable triple bond; n is an integer of 1 to 3; when n is 1, $R^1$ and $R^2$ may be bonded to each other; $X^1$ is a monovalent organic main group element group having a tellurium element, an antimony element or a bismuth element or an iodo group.

In this description, non-addition-polymerizable double bonds (hereinafter, also simply referred to as non-polymerizable double bonds) and non-addition-polymerizable triple bonds (hereinafter, also simply referred to as non-polymerizable triple bonds) are unsaturated bonds except addition-polymerizable unsaturated bonds (addition-polymerizable carbon-carbon double bonds and addition-polymerizable carbon-carbon triple bonds, respectively); examples of the non-addition-polymerizable double bonds and the non-addition-polymerizable triple bonds include a carbon-oxygen double bond contained in a carbonyl group, a carbon-nitrogen triple bond contained in a nitrile group, carbon-carbon double bonds that constitute aromatic hydrocarbons, and oxygen-nitrogen double bonds and carbon-nitrogen double bonds that constitute heteroaromatic compounds, and especially, a carbon-oxygen double bond contained in a carbonyl group, a carbon-nitrogen triple bond contained in a nitrile group, and carbon-carbon double bonds that constitute aromatic hydrocarbons are preferred.

When $R^1$ and $R^2$ are saturated hydrocarbon groups having 1 to 7 carbon atoms, examples of the saturated hydrocarbon groups having 1 to 7 carbon atoms include linear saturated hydrocarbon groups having 1 to 7 carbon atoms (e.g., methyl group, ethyl group, n-propyl group, n-butyl group, n-pentyl group, and n-hexyl group) and branched saturated hydrocarbon groups having 1 to 7 carbon atoms (e.g., i-propyl group, isobutyl group, s-butyl group, t-butyl group, isopentyl group, neopentyl group, t-pentyl group, 1-methylbutyl group, isohexyl group, s-hexyl group, t-hexyl group, neohexyl group, and heptyl group). Especially, linear saturated hydrocarbon groups having 1 to 5 carbon atoms are preferred from the viewpoint of solubility, polymerizability, etc., and linear saturated hydrocarbon groups having 1 to 3 carbon atoms are more preferred.

When $R^1$ and $R^2$ are monovalent groups having 1 to 7 carbon atoms and having at least one non-addition-polymerizable double bond or at least one non-addition-polymerizable triple bond, preferable groups include carboxy (salt) group (1 carbon atom, carbon-oxygen double bond), phenyl group (6 carbon atoms, non-polymerizable carbon-carbon double bond), cyano group (1 carbon atom, carbon-nitrogen triple bond), cyanomethyl group (2 carbon atoms, carbon-nitrogen triple bond), cyanoethyl group (3 carbon atoms, carbon-nitrogen triple bond), cyanopropyl group (4 carbon atoms, carbon-nitrogen triple bond), cyanobutyl group (5 carbon atoms, carbon-nitrogen triple bond), cyanopentyl group (6 carbon atoms, carbon-nitrogen triple bond), cyanohexyl group (7 carbon atoms, carbon-nitrogen triple bond), carboxymethyl group (2 carbon atoms, carbon-oxygen double bond), carboxyethyl group (3 carbon atoms, carbon-oxygen double bond), carboxypropyl group (4 carbon atoms, carbon-oxygen double bond), carboxybutyl group (5 carbon atoms, carbon-oxygen double bond), carboxypentyl group (6 carbon atoms, carbon-oxygen double bond), carboxyhexyl group (7 carbon atoms, carbon-oxygen double bond), benzyl group (7 carbon atoms, non-polymerizable carbon-carbon double bond), methoxycarbonyl group (2 carbon atoms, carbon-oxygen double bond), ethoxycarbonyl group (3 carbon atoms, carbon-oxygen double bond), propyloxycarbonyl group (4 carbon atoms, carbon-oxygen double bond), butyloxycarbonyl group (5 carbon atoms, carbon-oxygen double bond), pentyloxycarbonyl group (6 carbon atoms, carbon-oxygen double bond), hexyloxycarbonyl group (7 carbon atoms, carbon-oxygen double bond), hydroxyethoxycarbonyl group (3 carbon atoms, carbon-oxygen double bond), hydroxypropyloxycarbonyl group (4 carbon atoms, carbon-oxygen double bond), hydroxybutyloxycarbonyl group (5 carbon atoms, carbon-oxygen double bond), hydroxypentyloxycarbonyl group (6 carbon atoms, carbon-oxygen double bond), and hydroxyhexyloxycarbonyl group (7 carbon atoms, carbon-oxygen double bond), etc., and more preferably, a carboxy (salt) group, a cyano group, a carboxymethyl group, and a carboxyethyl group are enumerated.

Examples of such salts include salts of alkali metal (lithium, sodium, potassium, etc.), salts of alkaline earth metal (magnesium, calcium, etc.), and ammonium ($NH_4$) salts. Among these salts, salts of alkali metals and ammonium salts are preferred from the viewpoint of absorption performance and the like, salts of alkali metals are more preferred, and sodium salts are particularly preferred.

$R^3$ is an n-valent saturated hydrocarbon group having 1 to 7 carbon atoms or an n-valent group having 2 to 12 carbon atoms and having at least one non-addition-polymerizable double bond or at least one non-addition-polymerizable triple bond, and n is an integer of 1 to 3.

Of the n-valent saturated hydrocarbon groups having 1 to 7 carbon atoms represented by $R^3$, examples of a monovalent saturated hydrocarbon group having 1 to 7 carbon atoms include linear saturated hydrocarbon groups having 1 to 7 carbon atoms (e.g., methyl group, ethyl group, n-propyl group, n-butyl group, n-pentyl group, n-hexyl group, and heptyl group) and branched saturated hydrocarbon groups having 1 to 7 carbon atoms (e.g., i-propyl group, isobutyl group, s-butyl group, t-butyl group, isopentyl group, neopentyl group, t-pentyl group, 1-methylbutyl group, isohexyl group, s-hexyl group, t-hexyl group, neohexyl group, and isoheptyl group).

Of the n-valent saturated hydrocarbon groups having 1 to 7 carbon atoms represented by $R^3$, examples of a divalent saturated hydrocarbon group having 1 to 7 carbon atoms include divalent linear saturated hydrocarbon groups having 1 to 7 carbon atoms (e.g., methylene group, ethylene group, propylene group, butylene group, pentene group, hexene group, and heptene group) and divalent branched saturated hydrocarbon groups having 1 to 7 carbon atoms (e.g., isopropylene group, isobutylene group, s-butylene group, t-butylene group, isopentylene group, neopentylene group, t-pentylene group, 1-methylbutylene group, isohexylene group, s-hexylene group, t-hexylene group, neohexylene group, and isoheptylene group).

Of the n-valent saturated hydrocarbon groups having 1 to 7 carbon atoms represented by $R^3$, examples of a trivalent saturated hydrocarbon group having 1 to 7 carbon atoms include methine group.

Of the n-valent saturated hydrocarbon groups having 1 to 7 carbon atoms represented by $R^3$, a methyl group, a methylene group, and a methine group are preferred, and a hydroxymethyl group and a methylene group are more preferred.

Of the n-valent groups having 2 to 12 carbon atoms and having at least one non-addition-polymerizable double bond or at least one non-addition-polymerizable triple bond as $R^3$, examples of a monovalent group include the same groups as those enumerated for R1 and $R^2$, and preferred examples are also the same.

When $R^3$ is a divalent group having 2 to 12 carbon atoms and having at least one non-polymerizable double bond or at least one non-polymerizable triple bond, preferable groups include benzenediyl group (6 carbon atoms, non-polymerizable carbon-carbon double bond), 1-methoxycarbonylcarbonyloxyethyleneoxycarbonyl group (6 carbon atoms, oxygen-oxygen double bond), a carbonyloxyethylenecarbonyl group (4 carbon atoms, oxygen-oxygen double bond), etc.

When $R^3$ is a trivalent group having 2 to 12 carbon atoms and having at least one non-polymerizable double bond or at least one non-polymerizable triple bond, preferable groups include benzenetriyl group (6 carbon atoms, non-polymerizable carbon-carbon double bond), 2-carbonyloxy-carbonyloxypropylenecarbonyl group (5 carbon atoms, oxygen-oxygen double bond), etc.

When n is 1, $R^1$ and $R^2$ may be bonded to each other, and preferred examples of a group having a ring structure to be formed by $R^1$ and $R^2$ bonded to each other include a γ-butyrolactonyl group and a fluorenyl group. A group in which $R^1$ and $R^2$ are bonded to each other to form a ring structure contains the carbon atoms to which $R^1$ and $R^2$ are attached in the ring structure.

$X^1$ is a monovalent organic main group element group having a tellurium element, an antimony element, or a bismuth element or an iodine group, and preferred examples thereof include a methyltellanyl group, a dimethylstibanyl group, a dimethylbismuthanyl group, and an iodine group. Especially, a methyltellanyl group and an iodine group are more preferred, and the most preferred is an iodine group.

Examples of the organic main group element compounds represented by formula (1) include 2-iodopropionitrile, 2-methyl-2-iodopropionitrile, α-iodobenzylcyanide, 2-iodopropionamide, ethyl-2-methyl-2-iodopropinate, methyl 2-methyl-iodopropionate, propyl 2-methyl-iodopropionate, butyl 2-methyl-iodopropionate, pentyl 2-methyl-iodopropionate, hydroxyethyl 2-methyl-iodopropionate, 2-methyl-2-iodopropionic acid (salt), 2-iodopropionic acid (salt), 2-iodoacetic acid (salt), methyl 2-iodoacetate, ethyl 2-iodoacetate, ethyl 2-iodopentanoate, methyl 2-iodopentanoate, 2-iodopentanoic acid (salt), 2-iodohexanoic acid (salt), 2-iodoheptanoic acid (salt), diethyl 2,5-diiodoadipate, 2,5-diiodoadipic acid (salt), dimethyl 2,6-diiodo-heptanedioate, 2,6-diiodoheptanedioic acid (salt), α-iodo-γ-butyrolactone, 2-iodoacetophenone, benzyl iodide, 2-iodo-2-phenylacetic acid (salt), methyl 2-iodo-2-phenylacetate, ethyl 2-iodo-2-phenylacetate, ethyl 2-iodo-2-(4'-methylphenyl) acetate, hydroxyethyl 2-iodo-2-phenylacetate, ethyl 2-iodo-2-(4'-nitrophenyl)acetate, 4-nitrobenzyl iodide, (1-iodoethyl)benzene, iododiphenylmethane, 9-iodo-9H-fluorene, p-xylylene diiodide, 1,4-bis(1'-iodoethyl)benzene, ethylene glycol bis(2-methyl-2-iodo-propinate), tris(2-methyl-iodopropionic acid)glycerol, 1,3,5-tris(1'-iodoethylbenzene), ethylene glycol bis(2-iodo-2-phenylacetate), 2-methyltellanylpropionitrile, 2-methyl-2-methyltellanylpropionitrile, α-methyltellanylbenzylcyanide, 2-methyltellanylpropionamide, ethyl-2-methyl-2-methyltellanyl propinate, methyl 2-methyl-methyltellanylpropionate, propyl 2-methyl-methyltellanylpropionate, butyl 2-methyl-methyltellanylpropionate, pentyl 2-methyl-methyltellanylpropionate, hydroxyethyl 2-methyl-methyltellanylpropionate, 2-methyl-2-methyltellanylpropionic acid (salt), 2-methyltellanylpropionic acid (salt), 2-methyltellanylacetic acid (salt), methyl 2-methyltellanylacetate, ethyl 2-methyltellanylacetate, ethyl 2-methyltellanylpentanoate, methyl 2-methyltellanylpentanoate, 2-methyltellanylpentanoic acid (salt), 2-methyltellanylhexanoic acid (salt), 2-methyltellanylheptanoic acid (salt), diethyl 2,5-dimethyltellanyladipate, 2,5-dimethyltellanyladipic acid (salt), dimethyl 2,6-dimethyltellanylheptanedioate, 2,6-dimethyltellanyl-heptanedioic acid (salt), α-methyltellanyl-gamma-butyrolactone, 2-methyltellanylacetophenone, benzyl iodide, 2-methyltellanyl-2- phenylacetic acid (salt), methyl 2-methyltellanyl-2-phenylacetate, ethyl 2-methyltellanyl-2-phenylacetate, ethyl 2-methyltellanyl-2-(4'-methylphenyl)acetate, hydroxyethyl 2-methyltellanyl-2-phenylacetate, ethyl 2-methyltellanyl-2-(4'-nitrophenyl)acetate, 4-nitrobenzyl iodide, (1-methyltellanylethyl)benzene, methyltellanyldiphenylmethane, 9-methyltellanyl-9H-fluorene, p-xylylenediiodide, 1,4-bis(1'-methyltellanylethyl)benzene, ethylene glycol bis(2-methyl-2-methyltellanyl-propinate), tris(2-methyl-methyltellanylpropionic acid) glycerol, 1,3,5-tris(1'-methyltellanylethylbenzene), ethylene glycol bis(2-methyltellanyl-2-phenylacetate), 2-dimethylstibanylpropionitrile, 2-methyl-2-dimethylstibanylpropionitrile, α-dimethylstibanylbenzylcyanide, 2-dimethylstibanylpropionamide, ethyl-2-methyl-2-dimethylstibanyl-propinate, methyl 2-methyl-dimethylstibanylpropionate, propyl 2-methyl-dimethylstibanylpropionate, butyl 2-methyl-dimethylstibanylpropionate, pentyl 2-methyl-dimethylstibanylpropionate, hydroxyethyl 2-methyl-dimethylstibanylpropionate, 2-methyl-2-dimethylstibanylpropionic acid (salt), 2-dimethylstibanylpropionic acid (salt), 2-dimethylstibanylacetic acid (salt), methyl 2-dimethylstibanylacetate, ethyl 2-dimethylstibanylacetate, ethyl 2-dimethylstibanylpentanoate, methyl 2-dimethylstibanylpentanoate, 2-dimethylstibanylpentanoic acid (salt), 2-dimethylstibanylhexanoic acid (salt), 2-dimethylstibanylheptanoic acid (salt), diethyl 2,5-didimethylstibanyladipate, 2,5-didimethylstibanyladipic acid (salt), dimethyl 2,6-didimethylstibanyl-heptanedioate, 2, 6-didimethylstibanyl-heptanedioic acid (salt), α-dimethylstibanyl-γ-butyrolactone, 2-dimethylstibanylacetophenone, benzyl iodide, 2-dimethylstibanyl-2-phenylacetic acid (salt), methyl 2-dimethylstibanyl-2-phenylacetate, ethyl 2-dimethylstibanyl-2-phenylacetate, ethyl 2-dimethylstibanyl-2-(4'-methylphenyl)acetate, hydroxyethyl 2-dimethylstibanyl-2-phenylacetate, ethyl 2-dimethylstibanyl-2-(4'-nitrophenyl)acetate, 4-nitrobenzyl iodide, (1-dimethylstibanylethyl)benzene, dimethyl stibanyldiphenylmethane, 9-dimethylstibanyl-9H-fluorene, p-xylylene diiodide, 1,4-bis(1'-dimethylstibanylethyl)benzene, ethylene glycol bis(2-methyl-2-dimethylstibanyl propinate), tris(2-methyl-dimethylstibanylpropionic acid)glycerol, 1,3,5-tris(1'-dimethylstibanylethylbenzene), ethylene glycol bis(2-dimethylstibanyl-2-phenylacetate), 2-dimethylbismuthanyl propionitrile, 2-methyl-2-dimethylbismuthanylpropionitrile, α-dimethylbismuthanylbenzylcyanide, 2-dimethylbismuthanylpropionamide, ethyl-2-methyl-2-dimethylbismuthanylpropinate, methyl 2-methyl-dimethylbismuthanylpropionate, propyl 2-methyl-dimethylbismuthanylpropionate, butyl 2-methyl-dimethylbismuthanylpropionate, pentyl 2-methyl-dimethylbismuthanylpropionate, hydroxyethyl 2-methyl-dimethylbismuthanyl propionate, 2-methyl-2-dimethylbismuthanylpropionic acid (salt), 2-dimethylbismuthanylpropionic acid (salt), 2-dimethylbismuthanylacetic acid (salt), methyl 2-dimethylbismuthanylacetate, ethyl 2-dimethylbismuthanylacetate, ethyl 2-dimethylbismuthanylpentanoate, methyl 2-dimethylbismuthanylpentanoate, 2-dimethylbismuthanylpentanoic acid (salt), 2-dimethylbismuthanylhexanoic acid (salt), 2-dimethylbismuthanylheptanoic acid (salt), diethyl 2,5-didimethylbismuthanyladipate, 2,5-didimethylbismuthanyladipic acid (salt), dimethyl 2,6-didimethylbismuthanylheptanedioate, 2,6-didimethylbismuthanylheptanedioic acid (salt), α-dimethylbismuthanyl-γ-butyrolactone, 2-dimethylbismuthanylacetophenone, benzyl iodide, 2-dimethylbismuthanyl-2-phenylacetic acid (salt), methyl 2-dimethylbismuthanyl-2-phenylacetate, ethyl 2-dimethylbismuthanyl-2-phenylacetate, ethyl 2-dimethylbismuthanyl-2-(4'-methylphenyl)acetate, hydroxyethyl 2-dimethylbismuthanyl-2-phenylacetate, ethyl 2-dimethylbismuthanyl-2-(4'-nitrophenyl)acetate, 4-nitrobenzyl iodide, (1-dimethylbismuthanylethyl)benzene, dimethylbismuthanyldiphenylmethane, 9-dimethylbismuthanyl-9H-fluorene, p-xylylene iodide, 1,4-bis(1'-dimethylbismuthanylethyl)benzene, ethylene glycol bis(2-methyl-2-dimethylbismuthanyl propinate), tris(2-methyl-dimethylbismuthanylpropionic acid) glycerol, 1,3,5-tris(1'-dimethylbismuthanylethylbenzene), ethylene glycol bis(2-dimethylbismuthanyl-2-phenylacetate), and particularly preferred are 2-methyl-2-iodopropionitrile, ethyl-2-methyl-2-iodinepropinate, 2-methyl-2-iodo-propionic acid (salt), 2-iodoacetic acid (salt), methyl 2-iodoacetate, diethyl 2,5-diiodoadipate, 2,5-diiodoadipic acid, ethylene glycol bis(2-methyl-2-iodo-propinate), ethylene glycol bis(2-iodo-2-phenylacetate), 2-methyltellanylpropionitrile, ethyl-2-methyl-2-methyltellanyl-propinate, diethyl 2,5-bismethyltellanyladipate, ethylene glycol bis(2-methyl-2-methyltellanyl-propinate), ethylene glycol bis(2-methyltellanyl-2 phenylacetate), 2-dimethylstibanylpropionitrile, ethyl-2-methyl-2-dimethylstibanyl-propinate, 2-dimethylbismuthanylpropionitrile, and ethyl-2-methyl-2-dimethylbismuthanylpropinate.

The amount of the organic main group element compound used is preferably 0.0005 to 0.1% by weight, and more preferably 0.005 to 0.05% by weight, based on the total weight of the above-mentioned monomers (a1) and (a2) or, when an additional vinyl monomer (a3) is used, the total of (a1) to (a3). If the amount of the organic main group element compound is less than 0.0005% by weight, there is a possibility that polymerization cannot be controlled sufficiently, and the effects of water retention and gel strength enhancement cannot be obtained. On the other hand, if the amount of the organic main group element compound exceeds 0.1% by weight, the amount of soluble components may increase because the molecular chain becomes too short and there is a possibility that economic efficiency is poor.

In the production method of the present invention, the step of polymerizing a monomer composition comprising a water-soluble vinyl monomer (a1) and/or a hydrolyzable vinyl monomer (a2) and a crosslinking agent (b) in the presence of the organic main group element compound described above may be any conventionally known method, and for example, conventional polymerization such as aqueous solution polymerization (adiabatic polymerization, film polymerization, spray polymerization, etc.; e.g., JP-A-55-133413) and reverse-phase suspension polymerization (e.g., JP-B-54-30710, JP-A-56-26909, and JP-A-1-5808) may be performed in the presence of the organic main group element compound described.

When performing aqueous polymerization, a mixed solvent comprising water and an organic solvent can be used. Examples of the organic solvent include methanol, ethanol, acetone, methyl ethyl ketone, N,N-dimethylformamide, dimethylsulfoxide, and mixtures of two or more thereof.

When performing aqueous solution polymerization, the amount (% by weight) of an organic solvent used is preferably 40 or less, and more preferably 30 or less, based on the weight of water.

When the polymerization method is a suspension polymerization method or an reverse-phase suspension polymerization method, polymerization may be carried out in the presence of a conventional dispersing agent or a conventional surfactant, if necessary. In the case of an reverse-phase suspension polymerization method, the polymerization can be carried out using a conventional hydrocarbon solvent such as xylene, n-hexane, and n-heptane.

Of the polymerization methods, the aqueous solution polymerization method is preferred because it does not need use of an organic solvent, etc. and because it is advantageous in production cost aspect, and an adiabatic aqueous solution polymerization method is more preferred in that a water-soluble absorbent resin having a large water retention capacity and a small amount of water-soluble components is obtained and that the temperature control during polymerization is unnecessary.

In the polymerization, the weight percent concentration of the monomer composition comprising the water-soluble vinyl monomer (a1) and/or the hydrolyzable vinyl monomer (a2), and when an additional vinyl monomer (a3) is used, (a1) to (a3), and the crosslinking agent (b) is preferably 20 to 55% relative to the total weight of the polymerization liquid at the initiation of the polymerization. When being lower than this range, production efficiency becomes poor, whereas when being higher than this range, it is impossible to obtain a sufficient gel strength.

In the polymerization of the monomer composition described above, a conventional radical initiator can be used, if necessary. Examples of the conventional radical initiator include azo compounds [e.g., azobisisobutyronitrile, azobiscyanovaleric acid, and 2,2'-azobis(amidinopropane) hydrochoride], inorganic peroxides (e.g., hydrogen peroxide, ammonium persulfate, potassium persulfate, and sodium persulfate), organic peroxides [benzoyl peroxide, di-t-butyl peroxide, cumene hydroperoxide, succinic acid peroxide, and di(2-ethoyethyl) peroxydicarbonate], redox catalysts (combinations of a reducing agent such as alkali metal sulfite or bisulfite, ammonium sulfite, ammonium bisulfite and ascorbic acid and an oxidizing agent such as alkali metal persulfates, ammonium persulfate, hydrogen peroxide, and an organic peroxides), and photoradical generators [e.g., 2,4,6-trimethylbenzoyl-diphenyl-phosphine oxide, 1-hydroxycyclohexyl-phenyl ketone-hydroxyalkylphenone, and α-aminoalkylphenone]. Such radical initiators may be used singly and two or more thereof may be used in combination.

The amount (% by weight) of the radical initiator used is preferably 0.0005 to 5, and more preferably 0.001 to 2, based on the total weight of the water-soluble vinyl monomer (a1) and the hydrolyzable vinyl monomer (a2), or when an additional vinyl monomer (a3) is used, (a1) to (a3).

The polymerization initiation temperature in polymerizing the monomer composition comprising the water-soluble vinyl monomer (a1) and/or the hydrolyzable vinyl monomer (a2) and the crosslinking agent (b) in the presence of the organic main group element compound described above is preferably 0 to 100° C. When being lower than this range, the polymerization liquid can be frozen and it is difficult to perform the production, whereas when being higher than this range, the temperature in polymerization is too high and a sufficient gel strength cannot be obtained.

By the above-mentioned step of performing polymerization, a hydrous gel of a crosslinked polymer (A) containing water is obtained, and the hydrous gel may be chopped. The size (longest diameter) of the chopped gel is preferably 50 μm to 10 cm, more preferably 100 μm to 2 cm, and particularly preferably 1 mm to 1 cm. When the size is within such ranges, dryability during a drying step is further improved.

Chopping can be carried out by a conventional method and chopping can be done by using a chopping machine (e.g., Bex Mill, rubber chopper, Pharma Mill, mincing machine, impact type pulverizer, roll type pulverizer), etc. If necessary, the thus-obtained aqueous gel polymer may be neutralized by mixing it with an alkali.

As the alkali, known one (gazette of Japan Patent No. 3205168, etc.) can be used. Of these, lithium hydroxide, sodium hydroxide, and potassium hydroxide are preferred from the viewpoint of water absorption performance; more preferred are sodium hydroxide and potassium hydroxide, and particularly preferred is sodium hydroxide. From the viewpoint of liquid permeation property, the neutralization ratio is preferably 50 to 100%, and more preferably 60 to 80%.

Preferably, the production method of the present invention includes a step of distilling water and/or an organic solvent out of the above-mentioned polymerized gel. As a method of distilling off water and or the organic solvent, a method of distilling (drying) it with hot blast having a temperature of 80 to 400° C., a thin film drying method using, e.g., a drum dryer heated at 100 to 230° C., a (heating) reduced pressure drying method, a freeze-drying method, a drying method using infrared radiation, decantation, filtration, etc. can be applied.

When a solvent (organic solvents, water, etc.) is used for polymerization, it is preferred to distill off the solvent after the polymerization. When an organic solvent is contained in the solvent, the content (% by weight) of the organic solvent after distillation, based on the weight of the crosslinked polymer (A), is preferably 0 to 10, more preferably 0 to 5, particularly preferably 0 to 3, and most preferably 0 to 1. When the content is within this range, the absorption performance of the water-absorbent resin particles is further improved.

When water is contained in the solvent, the content (% by weight) of water after distillation is preferably 0 to 20, more preferably 0.5 to 10, particularly preferably 1 to 9, and most preferably 2 to 8, based on the weight of the crosslinked polymer (A). Within such ranges, the absorption performance is further improved.

The contents of an organic solvent and water can be determined from the weight loss of a sample when heating it with an infrared moisture content analyzer {e.g., JE400 manufactured by KETT; 120±5° C., 30 minutes, atmosphere humidity before heating: 50±10% RH, lamp specification: 100 V, 40 W}, but the determination is not limited to this.

The production method of the present invention preferably includes a step of pulverizing the aqueous gel after distilling water therefrom, and water-absorbent resin particles are obtained by the pulverization. The method of pulverization is not particularly limited and pulverizing apparatuses (e.g., hammer type pulverizer, impact type pulverizer, roll type pulverizer, and jet stream type pulverizer) can be used. The water-absorbent resin particles obtained by the pulverization can be adjusted in their particle size by sieving, etc., according to need.

The weight average particle diameter (μm) when having been sieved according to need is preferably 100 to 800, more preferably 200 to 700, even more preferably 250 to 600, particularly preferably 300 to 500, and most preferably 350 to 450. Within such ranges, the absorption performance is further improved.

The weight average particle diameter is measured by the method disclosed in Perry's Chemical Engineers' Handbook, Sixth Edition (McGraw-Hill Book Company, 1984, page 21) by using a RO-TAP sieve shaker and standard sieves (JIS Z8801-1:2006). Specifically, JIS standard sieves are combined, for example, in the order of 1000 μm, 850 μm, 710 µm, 500 µm, 425 µm, 355 µm, 250 µm, 150 µm, 125 µm, 75 µm, 45 µm, and a bottom tray when viewed from the top. About 50 g of particles to be measured are put on the top sieve and then shaken for five minutes by a RO-TAP sieve shaker. Then, the particles received on the respective sieves and the bottom tray are weighed and the weight fractions of the particles on the respective sieves are calculated with the total weight of the particles considered to be 100% by weight. The calculated values are plotted on a logarithmic probability sheet {taking the size of openings of a sieve (particle diameter) as abscissa and the weight fraction as ordinate} and then a line connecting the respective points is drawn. Subsequently, a particle diameter that corresponds to a weight fraction of 50% by weight is determined and this is defined as a weight average particle diameter.

Since a smaller content of particulates contained results in better absorption performance, the content (% by weight) of the particulates being 106 µm or less in size (preferably being 150 µm or less in size) that accounts for in the total weight of the crosslinked polymer (A) is preferably 3 or less, and more preferably 1 or less. The content of the particulates can be determined using a graph produced when determining the aforementioned weight average particle diameter.

The shape of the particle after performing the step of pulverization is not particularly limited and may be an irregularly pulverized form, a scaly form, a pearl-like form, a rice grain form, etc. Among these, an irregularly pulverized form is preferred because good entangling with a fibrous material in an application such as disposable diaper is ensured and the fear of falling off from the fibrous material is eliminated.

In the production method of the present invention, the crosslinked polymer (A) or the aqueous gel may, if necessary, be treated with a hydrophobic substance by the method disclosed in JP-A-2013-231199, or the like.

Preferably, the production method of the present invention includes a step of further surface-crosslinking the crosslinked polymer (A). By surface-crosslinking, it is possible to further enhance gel strength and it is possible to satisfy a desirable water retention capacity and an amount of absorption under load in practical use.

A method for surface-crosslinking the crosslinked polymer (A) may be a conventional method, e.g., a method in which a water-absorbent resin is processed into a particle form, and then is mixed with a mixed solution of a surface-crosslinking agent (d), water and a solvent and then heating reaction is performed. A method of the mixing may be spraying the above-mentioned mixed solution to the crosslinked polymer (A), dipping the crosslinked polymer (A) in the above-mentioned mixed solution, or the like, and preferred is a method of spraying the above-mentioned mixed solution to crosslinked polymer (A) and then mixing them.

Examples of the surface crosslinking agent (d) include polyglycidyl compounds, such as ethylene glycol diglycidyl ether, glycerol diglycidyl ether, and polyglycerol polyglycidyl ether; polyhydric alcohols, such as glycerol and ethylene glycol; ethylene carbonate, polyamines, and polyvalent metal compounds. Of these, preferred in that a crosslinking reaction can be performed at a relatively low temperature are the polyglycidyl compounds. Such surface crosslinking agents may be used singly or two or more of them may be used in combination.

The amount of the surface crosslinking agent (d) used is preferably 0.001 to 5% by weight, and more preferably 0.005 to 2% by weight, based on the weight of the water-absorbent resin before crosslinking. When the amount of the surface crosslinking agent (d) used is less than 0.001% by weight, there is a possibility that the degree of surface crosslinking the surface is not high enough and the effect of increasing the amount of absorption under load is insufficient. On the other hand, when the amount of (d) used exceeds 5% by weight, there is a possibility that the degree of crosslinking of a surface is excessively high and the water retention capacity lowers.

The amount of water used during surface crosslinking is preferably 1 to 10% by weight, and more preferably 2 to 7% by weight, based on the weight of the water-absorbent resin before crosslinking. When the amount of the water used is less than 1% by weight, there is a possibility that the degree of permeation of the surface-crosslinking agent (d) to the inside of water-absorbent resin particles is not high enough and the effect of increasing the amount of absorption under load is insufficient. On the other hand, if the amount of water used exceeds 10% by weight, there is a possibility that the permeation of the surface-crosslinking agent (d) to the inside is excessively high and the water retention capacity lowers though the increasing amount of absorption under load is observed.

As a solvent to be used together with water for surface-crosslinking, a conventional solvent can be used through appropriate selection taking into account the degree of permeation of the surface-crosslinking agent (d) into the water-absorbent resin particles, the reactivity of the surface-crosslinking agent (d), and preferably, the solvent is a hydrophilic organic solvent that is soluble in water, such as methanol and diethylene glycol. Solvents may be used singly or two or more of them may be used in combination.

The amount of the solvent used may be appropriately adjusted depending on the type of the solvent, and it is preferably 1 to 10% by weight based on the weight of the water-absorbent resin before surface-crosslinking. The ratio of the solvent to water may also be arbitrarily adjusted, and it is preferably 20 to 80% by weight, and more preferably 30 to 70% by weight on weight basis.

In order to perform surface-crosslinking, the mixed solution of the surface-crosslinking agent (d), water and the solvent is mixed with water-absorbent resin particles, and then heating reaction is performed. The reaction temperature is preferably 100 to 230° C., and more preferably 120 to 160° C. The reaction time can appropriately be adjusted depending on the reaction temperature, and it is preferably 3 to 60 minutes, and more preferably 10 to 40 minutes. The particulate water-absorbent resin obtained by surface-crosslinking may further be surface-crosslinked using a surface-crosslinking agent of the same type as or a different type from the surface-crosslinking agent used first.

After the surface-crosslinking, a step of adjusting the particle size by sieving may be performed, if necessary. The weight-average particle diameter of the particles obtained after the particle size adjustment is preferably 100 to 600 µm, and more preferably 200 to 500 µm. The content of particulates is preferred to be as small as possible; the content of particulates being equal to or smaller than 100 µm is preferably 3% by weight or less, and it is more preferred that the content of particulates being equal to or smaller than 150 µm be 3% by weight or less.

In the production method of the present invention, antiseptics, antifungal agents, antibacterial agents, antioxidants, UV absorbers, antioxidants, coloring agents, aromatics, deodorants, liquid permeation improvers, inorganic powders, organic fibrous materials, etc. may be added at an arbitrary stage, and the amount thereof is 5% by weight or less based on the weight of the water-absorbent resin obtained. Moreover, treatment to form a foamed structure may be performed at an arbitrary stage in the method of the present invention, if necessary, and granulation and molding may also be performed.

The apparent density (g/ml) of the water-absorbent resin particles obtained by the production method of the present invention is preferably 0.54 to 0.70, more preferably 0.56 to 0.65, and particularly preferably 0.58 to 0.60. Within such ranges, the skin irritation resistance of an absorbent article is further improved. The apparent density can be measured at 25° C. in accordance with JIS K7365:1999, for example.

The content of at least one main group element selected from among iodine, tellurium, antimony and bismuth contained in the water-absorbent resin particles is 0.0005 to 0.1% by weight relative to the weight of the water-absorbent resin particles. When the content is less than the range, water retention capacity is low, whereas when the content is larger than the range, it is un-economical. That content is preferably 0.002 to 0.05% by weight.

The chemical state of at least one main group element selected from the group consisting of iodine, tellurium, antimony, and bismuth is not particularly limited; however, the at least one main group element selected from the group consisting of iodine, tellurium, antimony, and bismuth preferably does not have oxidative power because water-absorbent resin particles tend to be colored with time when the at least one main group element has oxidative power.

Specific examples of the water-absorbent resin particles of the present invention include water-absorbent resin particles obtained by the above-mentioned the production method of the present invention or water-absorbent resin particles obtained by mixing a crosslinked polymer (A) produced by polymerization in the absence of an organic main group element compound and a compound comprising at least one main group element selected from the group consisting of iodine, tellurium, antimony, and bismuth.

As the disclosures on the polymerization, chopping, distilling off of water and/or a solvent, and pulverization of the hydrous gel of the crosslinked polymer (A) produced by polymerization in the absence of an organic main group element compound, the corresponding disclosures for the crosslinked polymer of the above-described production method of the present invention are incorporated herein by reference. The disclosures on the treatment with a hydrophobic substance and the surface-crosslinking of the crosslinked polymer (A) or the above-described hydrous gel for the crosslinked polymer of the above-described production method of the present invention are incorporated herein by reference. Moreover, the disclosures on the addition of antiseptics, antifungal agents, antibacterial agents, antioxidants, UV absorbers, antioxidants, coloring agents, aromatics, deodorants, liquid permeation improvers, inorganic powders, organic fibrous materials, etc. for the crosslinked polymer of the above-described production method of the present invention are incorporated herein by reference. The disclosure on the apparent density of water-absorbent resin particles for the crosslinked polymer of the above-described production method of the present invention is incorporated herein by reference.

A method of mixing the crosslinked polymer (A) with the main group element compound is not particularly limited and, for example, there can be used a method of mixing the crosslinked polymer (A) with the main group element compound using such a mixing apparatus as a cylindrical mixer, a screw type mixer, a screw type extruder, a Turbulizer, a Nauter mixer, a double-arm kneader, a fluidization mixer, a V-type mixer, a mincing mixer, a ribbon mixer, a fluidization mixer, an air mixer, a rotating disc mixer, a conical blender, and a roll mixer. Moreover, as a method of polymerizing the above-described monomer composition in the presence of the main group element compound, the above-described production method of the present invention can be used preferably. In this case, in the above-described production method of the present invention, at least one main group element selected from the group consisting of iodine, tellurium, antimony, and bismuth can be contained in an amount of 0.0005 to 0.1% by weight on the basis of the weight of the water-absorbent resin particles by adjusting the amount of the main group element compound used. A person skilled in the art can practice the production method appropriately with reference to, for example, Examples.

The water-absorbent resin particles of the present invention and water-absorbent resin particles obtained by the method for producing water-absorbent resin particles of the present invention (hereinafter simply referred to as water-absorbent resin particles or the water-absorbent resin particles of the present invention without distinguishing them) may be used solely as an absorbent or alternatively may be used as an absorbent together with another material.

Examples of the another material include a fibrous material. The structure and the production method of the absorbent or the like in the case of using together with a fibrous material are analogous to conventional structures and methods (JP-A-2003-225565, JP-A-2006-131767, JP-A-2005-097569, etc.).

Preferred as the fibrous material are cellulosic fiber, organic synthetic fiber and mixtures of a cellulosic fiber and an organic synthetic fiber.

Examples of the cellulosic fiber include natural fibers such as fluff pulp and cellulosic chemical fibers such as viscose rayon, acetate rayon, and cuprammonium rayon. Such cellulosic natural fibers are not particularly limited with respect to their source material (needle-leaf trees, broadleaf trees, etc.), production method (chemical pulp, semichemical pulp, mechanical pulp, CTMP, etc.), bleaching method, etc.

Examples of the organic synthetic fiber include polypropylene-based fiber, polyethylene-based fiber, polyamide-based fiber, polyacrylonitrile-based fiber, polyester-based fiber, polyvinyl alcohol-based fiber, polyurethan-based e fiber, and heat-weldable composite fiber (fiber in which at least two of the fibers differing in melting point are hybridized in a sheath-core type, an eccentric type, a parallel type, or the like, fiber in which at least two of the fibers are blended, and fiber in which the surface layer of said fibers is modified, etc.).

Preferred among these fibrous base materials are cellulosic natural fiber, polypropylene-based fiber, polyethylene-based fiber, polyester-based fiber, heat-weldable composite fiber, and mixed fiber thereof, and fluff pulp, heat-weldable composite fiber, and mixed fiber thereof are more preferred in that a resulting water absorber is excellent in shape retention after water absorption.

The fibrous material is not particularly limited in length and thickness, and it can suitably be used if its length is within a range of 1 to 200 mm and its thickness is within a range of 0.1 to 100 deniers. The shape thereof is also not particularly limited if it is fibrous, and examples of the shape include a narrow cylindrical form, a split yarn form, a staple form, a filament form, and a web form.

When the water-absorbent resin particles are processed together with a fibrous material to form an absorbent, the weight ratio of the water-absorbent resin particles to the fiber (the weight of the water-absorbent resin particles/the weight of the fiber) is preferably from 40/60 to 90/10, and more preferably from 70/30 to 80/20.

The absorbent comprising the water-absorbent resin particles described above can be used as an absorbent article. The absorbent article can be applied not only as sanitary goods such as disposable diaper or sanitary napkin but also as items to be used for various applications such as absorbent materials or retention materials for various types of aqueous liquid, a gelling agent, etc., which are disclosed later. The method for producing the absorbent article is analogous to conventional methods (those disclosed in JP-A-2003-225565, JP-A-2006-131767, and JP-A-2005-097569, etc.).

EXAMPLES

The present invention is further described below by means of Examples and Comparative Examples, but the present invention is not limited thereto. Hereafter, unless otherwise stated, "part (s)" means "part (s) by weight" and "%" means "% by weight." The concentration of atoms contained in absorbent resin particles, the gel strength of absorbent resin particles, the water retention capacity to a physiological saline, the amount of absorption under load, and the gel liquid permeation rate were measured by the following methods.

<Method for Measuring the Amount of an Element Contained in Water-Absorbent Resin Particles>

Five grams of a water-absorbent resin was pulverized with a high-speed vibration sample mill manufactured by CMT Co., Ltd., and then was pressed in a Briquestting Ring (made of vinyl chloride, 35 mm in diameter, 5 mm in thickness) to form a pellet by using a Briquest Press MP-35 manufactured by Shimadzu Corporation, and the concentration of atoms was determined using a semiquantitative analytical method using quantitative analysis software Uniquant while conditioning a full-automatic wavelength dispersive fluorescent X-ray spectrometer (device name: Axios, manufacturer: PANalytical) to X-ray excitation conditions including a voltage of 50 kV and a current of 40 mA, and a measuring chamber atmosphere: vacuum.

<Method for Measuring Gel Strength>

A 100-ml beaker was charged with 1.000 g of a water-absorbent resin and 30.00 g of physiological saline (an ion-exchanged water solution with a NaCl concentration of 0.90%) was added, followed by leaving at rest for 30 minutes so that the water-absorbent resin might be flattened by shaking the beaker slowly, and thus a 30-fold swollen measurement sample was prepared. Measurement was performed using a curd meter (manufactured by Itec Techno Engineering K.K., product name: Curd-Meter MAX ME-500) under conditions including an elevation rate of 1 inch/7 seconds, a pressure-sensitive shaft diameter of 8 φ, and a load of 100 g, and a breaking force applied at the point where the measured curve started to drop from a 45-degrees diagonal line was read, and the number average value of three measurements was taken as a gel strength.

<Method for Measuring Water Retention Capacity>

1.00 g of a measurement sample was put into a tea bag (20 cm long, 10 cm wide) made of nylon net with an opening size of 63 μm (JIS Z8801-1:2006) and then was immersed in 1,000 ml of physiological saline (salt concentration: 0.9%) for 1 hour without stirring, followed by pulling up and draining off water by hanging the sample for 15 minutes. Then, the sample in the tea bag was put in a centrifuge and centrifugally dewatered at 150 G for 90 seconds, thereby removing excess physiological saline. Subsequently, the weight (h1) of the sample including the tea bag was measured and then a water retention capacity was calculated from the following formula. (h2) is the weight of the tea bag measured with no measurement sample by analogous procedures to those described above. The temperature of the physiological saline used and that of the measurement atmosphere were 25° C.±2° C. Water retention capacity (g/g)=(h1)−(h2)

<Method for Measuring the Amount of Absorption Under Load>

Into a cylindrical plastic tube (inner diameter: 25 mm, height: 34 mm) with a nylon net having a mesh opening of 63 μm (JIS Z8801-1:2006) attached to the bottom of the tube, there was weighed 0.16 g of a measurement sample sieved into a range of 250 to 500 μm using a 30 mesh sieve and a 60 mesh sieve, and then the cylindrical plastic tube was made to stand vertically and the measurement sample was leveled to have an almost uniform thickness on the nylon net and then a balance weight (weight: 310.6 g, outer diameter: 24.5 mm) was put on the measurement sample. The weight (M1) of the cylindrical plastic tube as the whole was measured, and then the cylindrical plastic tube containing the measurement sample and the balance weight was made to stand in a petri dish (diameter: 12 cm) containing 60 ml of physiological saline (salt concentration: 0.9%) and was immersed with the nylon net side facing down and was left standing for 60 minutes. After a lapse of 60 minutes, the cylindrical plastic tube was pulled up from the petri dish and then was inclined to collect the water attaching to the bottom of the tube to drip in the form of water drops, thereby removing excess water. Then, the weight (M2) of the cylindrical plastic tube containing the measurement sample and the balance weight as the whole was measured and then the amount of absorption under load was determined from the following formula. The temperature of the physiological saline used and that of the measurement atmosphere were 25° C.±2° C. The amount (g/g) of absorption under load={(M2)−(M1)}/0.16

<Method for Measuring Gel Liquid Permeation Rate>

Figure 2:
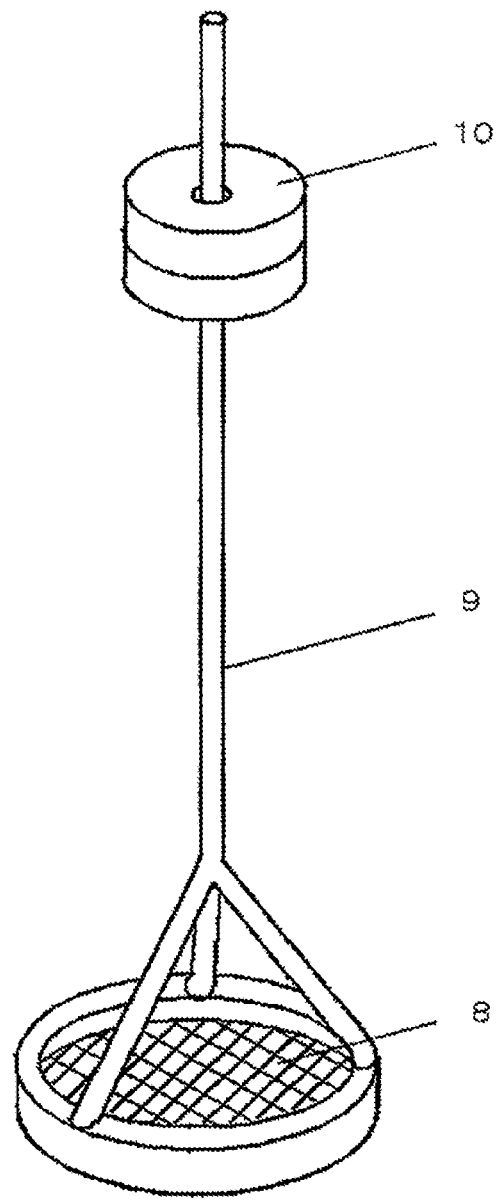
FIG. 2 is a perspective view schematically illustrating a pressing axis and weights for measuring a gel liquid permeation rate.

The gel liquid permeation rate was measured by the following operations using the instruments illustrated in FIG. 1 and FIG. 2.

Swollen gel particles 2 are prepared by immersing 0.32 g of a measurement sample in 150 ml of physiological saline 1 (salt concentration: 0.9%) for 30 minutes. Then, into a filtration cylinder equipped with a wire gauze 6 (mesh opening: 106 μm, JIS Z8801-1:2006) and a freely openable and closable cock 7 (inner diameter of the liquid passing portion: 5 mm) at the bottom of a vertically standing cylinder 3 {diameter (inner diameter): 25.4 mm, length: 40 cm; there were graduation lines 4 and 5 at the positions of 60 ml and 40 ml from the bottom, respectively}, the prepared swollen gel particles 2 are transferred together with the physiological saline while closing the cock 7. Then, a pressing axis 9 (weight: 22 g, length: 47 cm) with a circular wire gauze 8 (mesh opening: 150 μm, diameter: 25 mm) attached perpendicularly with respect to the wire gauze plane is put on the swollen gel particles 2 in such a manner that the wire gauze comes into contact with the swollen gel particles, and then a weight 10 (88.5 g) is put on the pressing axis 9 and is left standing for 1 minute. Subsequently, the cock 7 is opened and the time (T1; second) taken by the surface in the filtration cylinder to move from the 60 ml graduation line 4 to the 40 ml graduation line 5 is measured, and a gel liquid permeation rate (ml/min) is determined from the following formula.

Gel liquid permeation rate (ml/min)=20 ml×60/($T1$-$T2$)

The temperature of the physiological saline and that of the measurement atmosphere were 25° C.±2° C., and T2 is the time measured by the same operation as described above for the case of using no measurement sample.

Example 1

By mixing 270 parts of acrylic acid, 0.88 parts of pentaerythritol triallyl ether as a crosslinking agent (produced by Daiso Co., Ltd.), 0.041 parts of 2-iodo-2-methylpropionitrile (product made from TCI) and 712 parts of ion-exchanged water, an aqueous solution of the monomers was prepared, and then the mixed solution was supplied to a polymerization vessel in which adiabatic polymerization can be performed. By introducing nitrogen gas into the solution, the amount of the oxygen dissolved in the solution was adjusted to less than or equal to 0.2 ppm and the solution temperature was adjusted to 5° C. To this polymerization solution were added and mixed 1.1 parts of a 1% aqueous solution of hydrogen peroxide, 2.0 parts of a 2% aqueous solution of ascorbic acid, and 13.5 parts of a 2% aqueous solution of 2,2'-azobisamidinopropane dihydrochloride. At about 1 hour after the confirmation of the rise in temperature indicating the initiation of polymerization, the temperature arrived substantially at equilibrium at 80° C., and then aging was performed for additional 5 hours, affording a hydrous gel-like polymer.

While chopping the hydrous gel-like polymer into chips using a meat chopper, 221 parts of a 49% aqueous solution of NaOH was added, converting about 72 mol % of the carboxyl groups in the polymer into sodium salt. The neutralized hydrous gel was through-dried to a water content of 4% under conditions including a supplied wind temperature of 150° C. and a wind speed of 1.5 m/sec using a through hot air dryer (manufactured by Inoue Kinzoku Kogyo Co., Ltd.). The dried material was pulverized with a juicing blender (OSTERIZER BLENDER manufactured by Oster) and then sieved to adjust it into a particle size range of from 710 to 150 μm, there by obtaining a water-absorbent resin (A1-1).

Example 2

A water-absorbent resin (A1-2) was obtained by performing the same operations as those of Example 1 except changing the quantity of 2-iodo-2-methylpropionitrile from 0.041 parts to 0.0054 parts in Example 1. The temperature achieved at the equilibrium was 80° C.

Example 3

A water-absorbent resin (A1-3) was obtained by performing the same operations as those of Example 1 except changing the quantity of pentaerythritol triallyl ether from 0.88 parts to 1.2 parts and changing the quantity of 2-iodo-2-methylpropionitrile from 0.041 parts to 0.22 parts in Example 1.

Example 4

In 60 mL of acetone were dissolved 7.2 g of diethyl 2,5-dibromoadipate (produced by TCI) and 6.6 g of sodium iodide (produced by Wako Pure Chemical Industries, Ltd.), followed by stirring at room temperature for 3 hours. Acetone was removed with a rotary evaporator and the residue was dissolved in diethyl ether, followed by liquid-separation washing with an aqueous solution of sodium thiosulfate. After removing the solvent with a rotary evaporator, the residue was dried under reduced pressure, affording diethyl 2,5-diiodoadipate.

A water-absorbent resin (A1-4) was obtained by performing the same operations as those of Example 1 except changing 2-iodo-2-methylpropionitrile to 0.041 parts of diethyl 2,5-diiodoadipate in Example 1.

Example 5

A water-absorbent resin (A1-5) was obtained by performing the same operations as those of Example 1 except changing 2-iodo-2-methylpropionitrile to 0.041 parts of ethyl-2-methyl-2-methyltellanyl-propionate (synthesized by a method disclosed in WO 2004/014848) in Example 1.

Example 6

A water-absorbent resin (A1-6) was obtained by performing the same operations as those of Example 1 except changing 2-iodo-2-methylpropionitrile to 0.041 parts of ethyl-2-methyl-2-dimethylstibanyl-propionate (synthesized by a method disclosed in WO 2006/001496) in Example 1.

Example 7

A water-absorbent resin (A1-7) was obtained by performing the same operations as those of Example 1 except changing 2-iodo-2-methylpropionitrile to 0.041 parts of methyl-2-methyl-2-dimethylbismuthanyl-propionate (synthesized by a method disclosed in WO 2006/062255) in Example 1.

Example 8

A water-absorbent resin (A1-8) was obtained by performing the same operations as those of Example 1 except changing the quantity of 2-iodo-2-methylpropionitrile in Example 1 to 0.015 parts.

Example 9

A water-absorbent resin (A1-9) was obtained by performing the same operations as those of Example 1 except changing the quantity of 2-iodo-2-methylpropionitrile to 0.09 parts and the quantity of the 1% aqueous solution of hydrogen peroxide in Example 1 to 0.5 parts.

Example 10

While stirring 100 parts of the water-absorbent resin (A1-1) (by using a high-speed stirring turbulizer manufactured by Hosokawa Micron Co.; rotation speed: 2000 rpm), a solution composed of 0.12 parts of ethylene glycol diglycidyl ether, 1.9 parts of water, 1.2 parts of propylene glycol, and 1.0 parts of Klebosol 30CAL25 (produced by Merck Ltd.) was added and mixed, and then surface-crosslinking was carried out by heating at 140° C. for 45 minutes, and thus a water-absorbent resin (A2-1) was obtained.

Examples 11 to 18

Water-absorbent resins (A2-2) to (A2-9) were obtained by performing the same operations as those in Example 10 except using water-absorbent resins (A1-2) to (A1-9) instead of water-absorbent resin (A1-1).

Comparative Example 1

A water-absorbent resin (R1-1) for comparison was obtained by performing the same operations as those of Example 1 except failing to use 2-iodo-2-methylpropionitrile in Example 1.

Comparative Example 2

A water-absorbent resin (R1-2) for comparison was obtained by performing the same operations as those of Example 1 except changing 2-iodo-2-methylpropionitrile to 0.22 parts of sodium hypophosphite (produced by Wako Pure Chemical Industries, Ltd.) in Example 1.

Comparative Example 3

A water-absorbent resin (R2-1) for comparison was obtained by performing the same operations as those of Example 10 except using water-absorbent resin (R1-1) for comparison instead of water-absorbent resin (A1-1).

Comparative Example 4

A water-absorbent resin (R2-2) for comparison was obtained by performing the same operations as those of Example 11 except using water-absorbent resin (R1-2) for comparison instead of water-absorbent resin (A1-2).

The evaluation results of water retention capacity, gel strength, and element content of the water-absorbent resins (A1-1) to (A1-9) and the water-absorbent resins (R1-1) to (R1-2) for comparison were shown in Table 1. N.D. in the table means Not Detectable.

Moreover, the evaluation results of water retention capacity, amount of absorption under load, and gel liquid permeation rate of the obtained water-absorbent resins (A2-1) to (A2-9) and the water-absorbent resins (R2-1) to (R2-2) for comparison were shown in Table 2.

TABLE 1

| | | Water-absorbent resin | Water retention capacity (g/g) | Gel strength (kN/m2) | Contained element | Element content (ppm) |
|---|---|---|---|---|---|---|
| Examples | 1 | (A1-1) | 65 | 1.4 | Iodine | 67 |
| | 2 | (A1-2) | 57 | 2.1 | Iodine | 8 |
| | 3 | (A1-3) | 64 | 1.4 | Iodine | 350 |
| | 4 | (A1-4) | 58 | 1.7 | Iodine | 56 |
| | 5 | (A1-5) | 61 | 1.6 | Tellurium | 64 |
| | 6 | (A1-6) | 62 | 1.5 | Antimony | 58 |
| | 7 | (A1-7) | 62 | 1.6 | Bismuth | 61 |
| | 8 | (A1-8) | 61 | 1.9 | Iodine | 25 |
| | 9 | (A1-9) | 63 | 1.5 | Iodine | 161 |
| Comparative Examples | 1 | Comparative water-absorbent resin (R1-1) | 53 | 1.9 | N.D. | N.D. |
| | 2 | Comparative water-absorbent resin (R1-2) | 56 | 1.4 | N.D. | N.D. |

TABLE 2

| | | Water-absorbent resin | Water retention capacity (g/g) | Amount of absorption under load (g/g) | Gel liquid permeation rate (ml/min) |
|---|---|---|---|---|---|
| Examples | 10 | (A2-1) | 43 | 20 | 30 |
| | 11 | (A2-2) | 40 | 22 | 48 |
| | 12 | (A2-3) | 43 | 20 | 29 |
| | 13 | (A2-4) | 41 | 21 | 35 |
| | 14 | (A2-5) | 43 | 21 | 31 |
| | 15 | (A2-6) | 42 | 22 | 32 |
| | 16 | (A2-7) | 43 | 21 | 28 |
| | 17 | (A2-8) | 41 | 22 | 34 |
| | 18 | (A2-9) | 42 | 22 | 32 |
| Comparative Examples | 3 | Comparative water-absorbent resin (R2-1) | 35 | 23 | 41 |
| | 4 | Comparative water-absorbent resin (R2-2) | 39 | 18 | 20 |

The results in Tables 1 and 2 show that the water-absorbent resins of the present invention are high in water retention capacity and gel strength as compared with the water-absorbent resins of Comparative Examples. In particular, the results in Table 2 show that as compared with the water-absorbent resins of Comparative Examples, the water-absorbent resins of the present invention were improved in the amount of absorption under load and gel liquid permeation to the same level or more while having superior water retention capacity and thus the absorption performance were far advanced.

INDUSTRIAL APPLICABILITY

The water-absorbent resin particles of the present invention can be compatible with the liquid permeability between swollen gel particles and the absorption performance under load and they can be processed by applying them to various types of absorbents to form absorbent articles having a large amount of absorption and being superior in rewet performance or surface dry feeling. Accordingly, they are suitably used for sanitary goods, such as disposable diapers (disposable diaper for children, disposable diaper for adults, etc.), napkins (sanitary napkin, etc.), paper towel, pads (incontinence pad, surgical underpad, etc.), and pet sheets (pet urine absorbing sheet), and is best suited for disposable diapers.

Moreover, the water-absorbent resin particles of the present invention are useful not only for sanitary goods but also for other various applications such as a pet urine absorbent, a urine gelatinizer of a portable toilet, an agent for preserving freshness of vegetables and fruits etc., a drip absorbent for meats and fishes, a refrigerant, a disposable air-activated warmer, a battery gelatinizer, a water retention agent for plants, soil, etc., a moisture condensation preventing agent, a waterproofing agent, a packing agent, artificial snow, etc.

DESCRIPTION OF REFERENCE SIGNS

1 Physiological saline
2 Hydrous gel particles
3 Cylinder
4 Graduation line at the position of 60 ml from the bottom
5 Graduation line at the position of 40 ml from the bottom
6 Wire gauze
7 Stop cock
8 Circular wire gauze
9 Pressing axis
10 Weight

The invention claimed is:
1. A method for producing water-absorbent resin particles, comprising a step of polymerizing a monomer composition consisting of a water-soluble vinyl monomer (a1) and/or a vinyl monomer (a2) that turns into a water-soluble vinyl monomer (a1) through hydrolysis and up to 5 mol % of an additional vinyl monomer (a3) copolymerizable with the aforementioned vinyl monomers (a1) and (a2) based on the total number of mols of the vinyl monomer (a1) and the vinyl monomer (a2) and a crosslinking agent (b) in the presence of at least one organic main group element compound selected from the group consisting of organic iodine compounds having a tertiary carbon atom to which an iodo group attaches, wherein the monomer composition contains at least one of acrylic acid, methacrylic acid, a salt of acrylic acid and a salt of methacrylic acid as the water-soluble vinyl monomer (a1) in an amount of at least 75 mol % based on the total number of moles of the vinyl monomer (a1) and the vinyl monomer (a2), wherein the method includes a step of surface-crosslinking the crosslinked polymer (A).

2. The method for producing a water-absorbent resin particle according to claim 1, wherein the organic main group element compound is represented by the following formula (1):

[Chemical Formula 1]

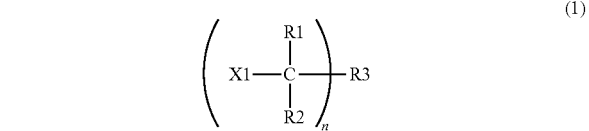

in the formula (1), $R^1$ and $R^2$ each independently represent a saturated hydrocarbon group having 1 to 7 carbon atoms, or a monovalent group having 1 to 7 carbon atoms and having at least one non-addition-polymerizable double bond or at least one non-addition-polymerizable triple bond and $R^3$ represents an n-valent saturated hydrocarbon group having 1 to 7 carbon atoms or an n-valent group having 2 to 12 carbon atoms and having at least one non-addition-polymerizable double bond or at least one non-addition-polymerizable triple bond, provided that at least one of $R^1$ to $R^3$ in one molecule is a corresponding group having a non-addition-polymerizable double bond or at least one non-addition-polymerizable triple bond; n is an integer of 1 to 3; when n is 1, $R^1$ and $R^2$ may be bonded to each other; $X^1$ is an iodo group.

3. The method for producing a water-absorbent resin particle according to claim 1, wherein the weight of organic iodine compounds is 0.0005 to 0.1% by weight relative to the total weight of the water-soluble vinyl monomer (a1) and the vinyl monomer (a2) that turns into a water-soluble vinyl monomer (a1) through hydrolysis.

4. The method for producing a water-absorbent resin particle according to claim 1, wherein the organic main group element compound is at least one selected from the group consisting of 2-methyl-2-iodopropionitrile, ethyl-2-methyl-2-iodopropinate, 2-methyl-2-iodopropionic acid (salt), ethylene glycol bis(2-methyl-2-iodo-propinate).

* * * * *